US007568379B2

(12) United States Patent
Simon et al.

(10) Patent No.: US 7,568,379 B2
(45) Date of Patent: Aug. 4, 2009

(54) METHOD OF MEASURING POROSITY BY MEANS OF ELLIPSOMETRY AND DEVICE FOR IMPLEMENTING ONE SUCH METHOD

(75) Inventors: Gurvan Simon, Grenoble (FR); Frédéric Ferrieu, Corenc (FR)

(73) Assignee: Commissariat a l'Energie Atomique, Paris (FR)

( * ) Notice: Subject to any disclaimer, the term of this patent is extended or adjusted under 35 U.S.C. 154(b) by 154 days.

(21) Appl. No.: 11/919,874

(22) PCT Filed: Apr. 28, 2006

(86) PCT No.: PCT/FR2006/000960

§ 371 (c)(1),
(2), (4) Date: Nov. 5, 2007

(87) PCT Pub. No.: WO2006/123030

PCT Pub. Date: Nov. 23, 2006

(65) Prior Publication Data

US 2009/0019921 A1    Jan. 22, 2009

(30) Foreign Application Priority Data

May 18, 2005  (FR) .................................. 05 04987

(51) Int. Cl.
*G01N 15/08* (2006.01)
(52) U.S. Cl. ..................... 73/38; 73/37; 438/7; 438/14; 438/16
(58) Field of Classification Search ..................... 73/37, 73/38; 438/7, 14, 16
See application file for complete search history.

(56) References Cited

U.S. PATENT DOCUMENTS

| 6,319,736 | B1 * | 11/2001 | Baklanov et al. ............... 438/16 |
| 6,435,008 | B2 * | 8/2002 | Baklanov et al. ............... 73/38 |
| 6,662,631 | B2 * | 12/2003 | Baklanov et al. ............... 73/38 |
| 6,831,742 | B1 | 12/2004 | Sui et al. |
| 6,986,280 | B2 * | 1/2006 | Muckenhirm ................ 73/104 |

(Continued)

FOREIGN PATENT DOCUMENTS

WO    WO 03/029789 A2    4/2003

OTHER PUBLICATIONS

Baklanov et al., "Determination of pore size distribution in thin films by ellipsometric porosimetry," *Journal of Vacuum Science and Technology B: Microelectronics Processing and Phenomena*, American Vacuum Society, vol. 18, No. 3, May 2000, pp. 1385-1391.

*Primary Examiner*—David A. Rogers
(74) *Attorney, Agent, or Firm*—Oliff & Berridge, PLC (57) ABSTRACT

The method for measuring the porosity of an element is performed by means of a measuring device comprising a measuring chamber in which the element is disposed, a solvent tank associated with an adsorption valve, and a pump associated with a desorption valve. The measuring method comprises measurement of the pressure in the chamber by means of a pressure sensor, and a cycle for measuring the porosity by ellipsometry at different predetermined pressure. During this measuring cycle, a pressure controller controls opening of the adsorption and desorption valves according to the measured pressure. The relative pressure in the chamber is successively regulated at different predetermined values, while maintaining a continuous flow of solvent in the chamber between the tank and the pump.

14 Claims, 5 Drawing Sheets

U.S. PATENT DOCUMENTS 7,421,885 B2 * 9/2008 Kitzhoffer et al. ............. 73/38
7,458,251 B2 * 12/2008 Baklanov et al. ............... 73/38
2001/0054306 A1 12/2001 Baklanov et al.
2002/0110921 A1 8/2002 Louwen et al.

* cited by examiner

METHOD OF MEASURING POROSITY BY MEANS OF ELLIPSOMETRY AND DEVICE FOR IMPLEMENTING ONE SUCH METHOD

BACKGROUND OF THE INVENTION

The invention relates to a method for measuring the porosity of an element by means of a device comprising:
- a measuring chamber in which the element is disposed,
- a solvent tank associated with an adsorption valve, arranged between the solvent tank and an inlet of the chamber,
- a pump associated with a desorption valve, arranged between an outlet of the chamber and the pump,
- a pressure sensor,
- control means for controlling the adsorption and desorption valves, the measuring method comprising measurement of the pressure in the chamber by means of the pressure sensor and a measuring cycle for measuring the porosity by ellipsometry, at different predetermined pressure or temperature values.

The invention also relates to a device implementing one such method.

STATE OF THE ART

The study of porous materials with low permittivity, called "low-k" materials, presents interests in a large number of fields, in particular in micro and nanotechnologies. Measurement of the different characteristics of the porosity of these materials can be performed for example by ellipsometric porosimetry.

Ellipsometric porosimetry enables the thickness and index of the porous layer to be measured in a solvent vapor environment. The variation of the refractive index of the porous layer as a function of the relative pressure of the solvent vapor enables the volume of solvent introduced into the open pores to be determined and an isothermal curve to be established. From this measurement, it is possible to determine different important characteristics of the porosity and therefore to control the electrical and mechanical properties of the porous material.

Figure 1:
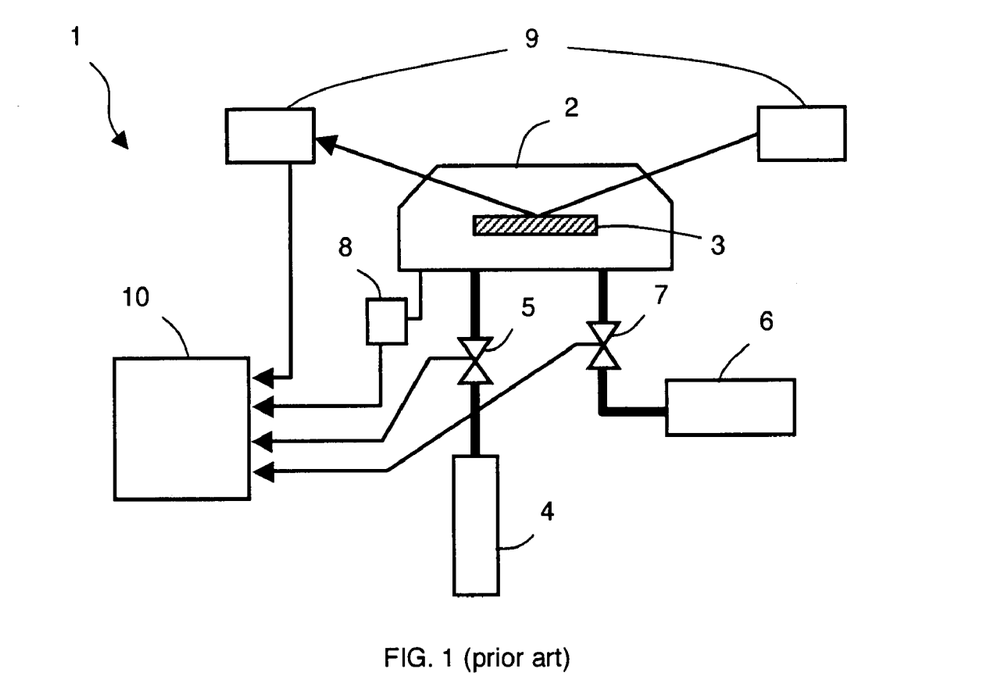
FIG. 1 represents a device for measuring porosity by ellipsometry according to the prior art.

To implement such a method of measuring by ellipsometric porosimetry, numerous laboratories have developed specific equipment. The documents U.S. Pat. Nos. 6,319,736 and 6,435,008 describe an example of a measuring device implementing one such method. As represented in FIG. 1, the measuring device 1 comprises a measuring chamber 2 inside which an element 3 formed by porous materials is disposed.

The device 1 comprises a solvent tank 4 associated with an adsorption valve 5 designed to inlet solvent to chamber 2, and a pump 6 associated with a desorption valve 7 designed to pump the solvent vapors. A pressure sensor 8 is connected to chamber 2 to measure the pressure inside the chamber 2. Measurement of the porosity is performed by means of an ellipsometer 9, which can be connected to a data recording system 10. The pressure sensor 8 and the adsorption valve 5 and desorption valve 7 can also be connected to the data recording system 10 to recover usable data.

Such a measuring device 1 manages and controls the pressure in "static" mode throughout a cycle for measuring porosity by ellipsometry, i.e. the pressure variations in chamber 2 are controlled either by supplying solvent to the chamber 2 or by pumping the solvent out.

Figure 3:
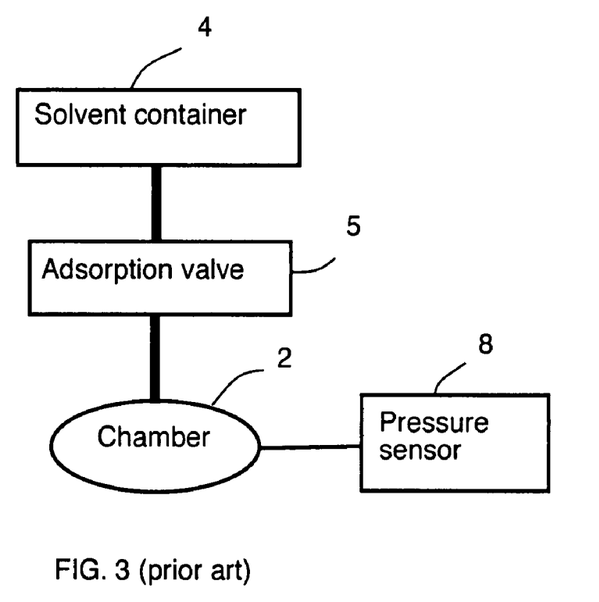
FIGS. 3 and 4 represent the device according to FIG. 1, respectively in the adsorption phase and in the desorption phase, in block diagram form.
Figure 4:
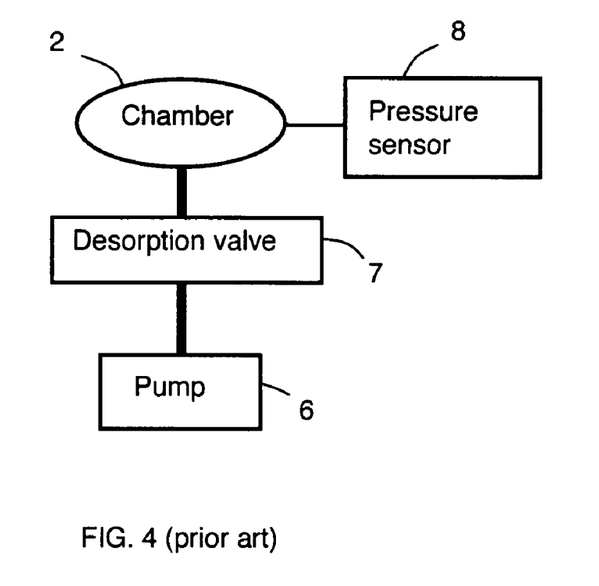

Referring to FIGS. 3 and 4 respectively illustrating a solvent adsorption phase and a solvent desorption phase, the pressure increase, or adsorption phase (FIG. 3), takes place solely by solvent vapor being supplied to the chamber 2 via the controlled adsorption valve 5, and the pressure decrease, or desorption phase (FIG. 4), takes place solely by pumping the solvent present in the chamber 2 through the controlled desorption valve 7 by means of the pump 6.

Figure 2:
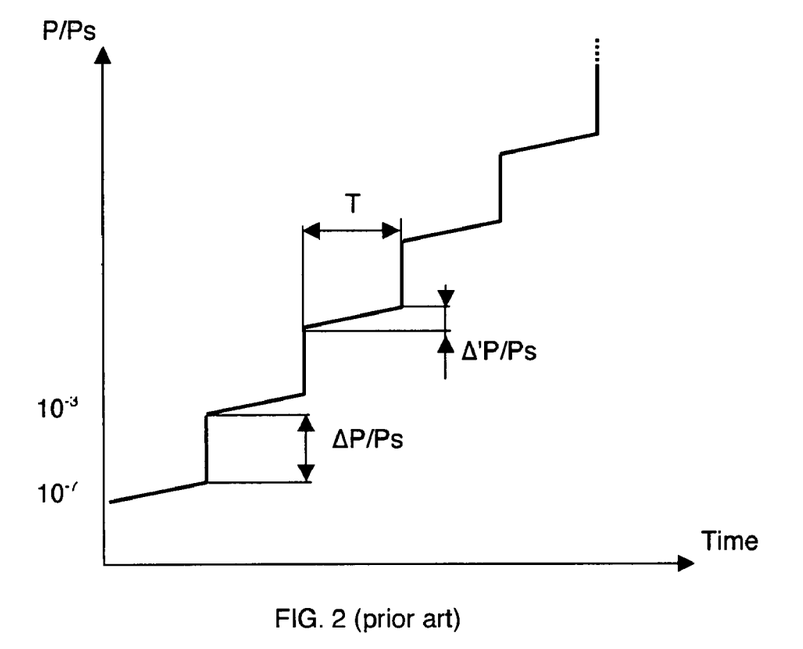
FIG. 2 is a graph of the pressure versus time illustrating the different predetermined pressure plateaus of the adsorption phase where the measurements are made, according to the prior art.

As represented in FIG. 2 illustrating the adsorption phase of a cycle for measuring porosity by ellipsometry, the measuring device 1 controls the adsorption valve 5 to obtain a plurality of successive pressure plateaus where the measurements are made. A pressure variation $\Delta'P/Ps$, where Ps is the saturated vapor pressure of the solvent, is observed at the level of a plateau throughout a measuring time T. This pressure variation originates on the one hand from the continuous inlet of solvent during the ellipsometry measurements, and on the other hand from leaks of certain parts of the measuring device in a vacuum. The results of the measurements are then obtained ignoring this pressure variation between the beginning and end of the measure.

This pressure variation $\Delta'P/Ps$ does however set problems, namely of imprecision of measurements and use of the results, and limits the gap between the pressure plateaus. Moreover, the isothermal curves obtained are not totally reliable and such a measuring device does not enable the range of low pressures to be mastered for studying the microporosity.

Control of the pressure by the adsorption 5 and desorption 7 valves can also cause temperature variations. Temperature variations can also be due to external conditions such as the temperature of the room in which the ellipsometric porosimetry measuring device is situated or to internal phenomena such as capillary condensation of the solvent on the walls of the open pores of the material.

In addition, the same physisorption phenomenon can give rise to temperature variations. But a temperature variation, even a small one, distorts the isothermal curves obtained by the ellipsometric measurements, which can then no longer be studied in detail.

Furthermore, pollution of element 3 inside chamber 2 by carbon residues of uncertain origin is commonly observed in all manipulations of the same type.

OBJECT OF THE INVENTION

One object of the invention is to remedy the shortcomings set out above and to provide a method for measuring porosity by ellipsometry, improving existing measuring methods by giving the measurements an optimal precision and enabling the results obtained to be used in dependable manner.

It is a further object of the invention to provide a device for implementing one such method of measuring porosity by ellipsometry.

These objects of the invention are achieved by the appended claims. The method according to the invention is more particularly characterized by the fact that, during the cycle for measuring porosity by ellipsometry, said control means control opening of the adsorption and desorption valves according to the measured pressure, the relative pressure in the chamber being successively regulated to different predetermined values, while maintaining a continuous flow of solvent in the chamber between the tank and the pump.

The device according to the invention is more particularly characterized by the fact that the adsorption and desorption valves are controlled in pressure or in position by means of the control means controlling opening of the valves.

BRIEF DESCRIPTION OF THE DRAWINGS

Other advantages and features will become more clearly apparent from the following description of particular embodiments of the invention given as non-restrictive examples only and represented in the accompanying drawings in which.

DESCRIPTION OF PARTICULAR EMBODIMENTS

Figure 5:
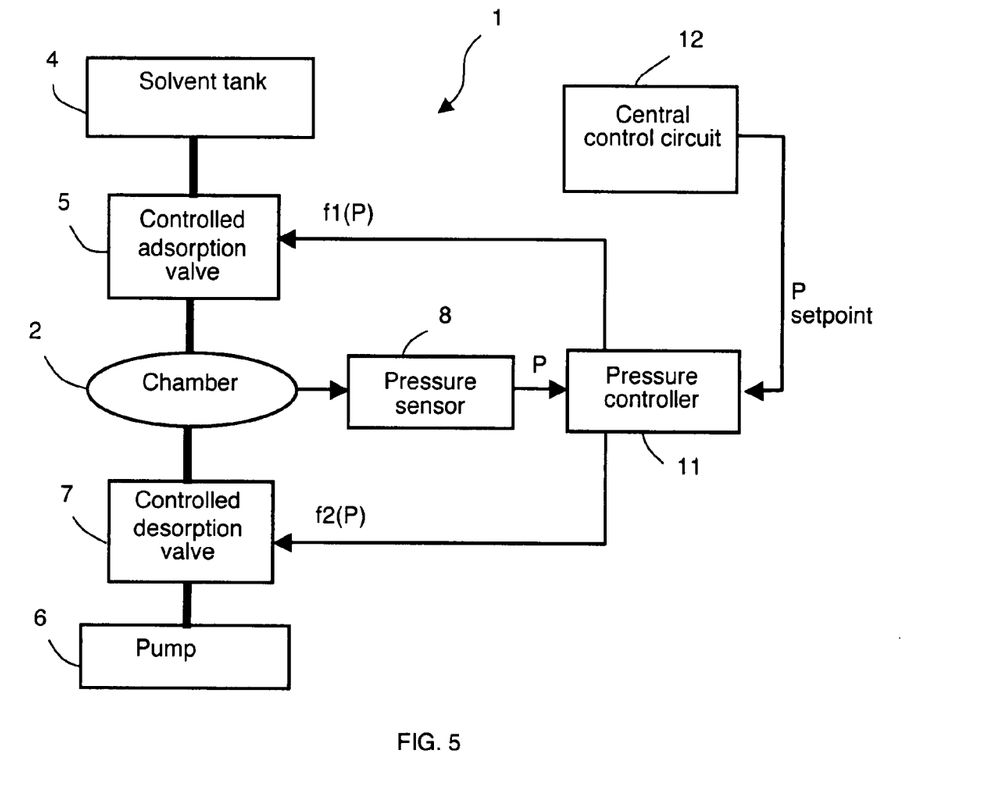
FIG. 5 represents a particular embodiment of a device for measuring porosity by ellipsometry according to the invention, in block diagram form.

In FIG. 5, the device 1 for measuring the porosity by ellipsometry of an element 3 in chamber 2 comprises the solvent tank 4 associated with the adsorption valve 5, and the pump 6 associated with the desorption valve 7. The adsorption valve 5 and desorption valve 7 are controlled by a pressure controller 11 connected to the pressure sensor 8 measuring the pressure inside chamber 2.

Depending on the pressure value P measured by sensor 8, the pressure controller 11 controls opening and closing of the adsorption valve 5 according to the function f1(P), and opening and closing of the desorption valve 7 according to the function f2(P). The pressure controller 11 is designed to maintain a continuous flow of solvent in chamber 2 between the solvent tank 4 and the pump 6. The pressure in chamber 2 is stabilized when the incoming quantity of solvent is equal to the outgoing quantity of solvent. Pressure regulation is performed according to the commands f1(P) and f2(P) so as to form successive different pressure plateaus during the cycle for measuring the porosity by ellipsometry.

Before starting the measuring cycle, the device 1 can preferably implement a pumping step of chamber 2, by means of the pump 6, until a relative vacuum is reached, acting as initial pressure for the measurements.

Figure 6:
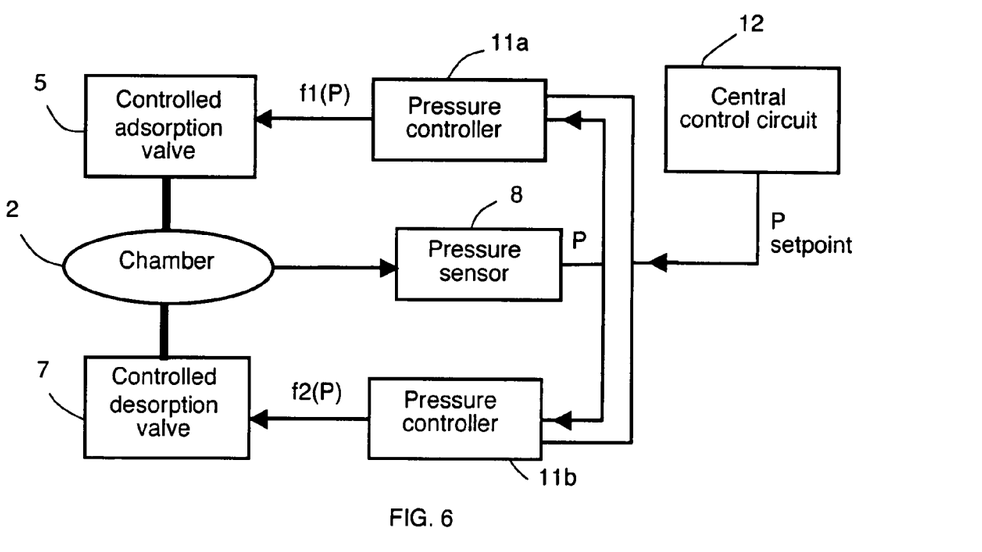
FIG. 6 represents an alternative embodiment of a device for measuring porosity by ellipsometry according to FIG. 5, in block diagram form.

In the alternative embodiment represented in FIG. 6, two pressure controllers 11a, 11b can be provided respectively connected to the adsorption valve 5 and to the desorption valve 7. Depending on the pressure value P measured by sensor 8, the pressure controller 11a controls opening and closing of the adsorption valve 5 according to the function f1(P) and the pressure controller 11b controls opening and closing of the desorption valve 7 according to the function f2(P).

Figure 7:
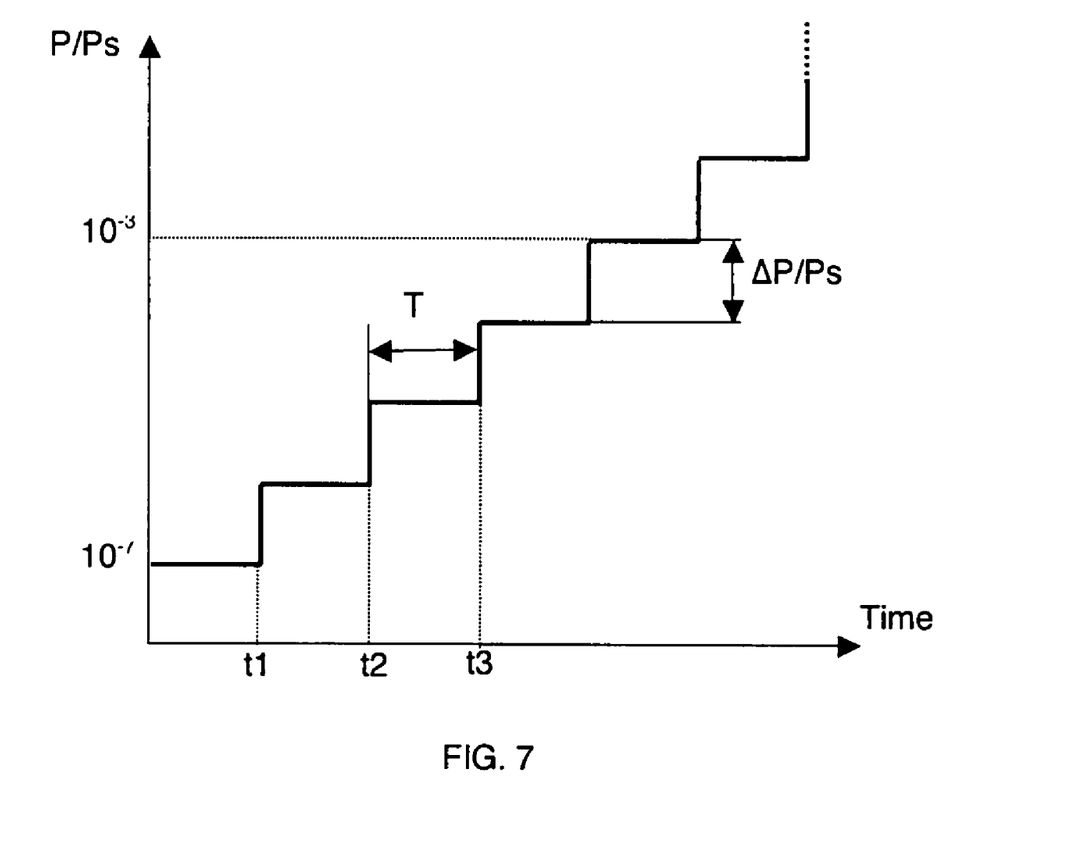
FIG. 7 is a graph of the pressure versus time illustrating the different predetermined pressure plateaus of the adsorption phase where the measurements are made, according to the invention.

FIG. 7 represents the relative pressure variations P/Ps versus time, where Ps is the solvent saturated vapor pressure. It can be determined for example by one of the following methods: measuring the pressure at the end of cycle, or measuring the room temperature and determining the pressure Ps according to the solvent temperature from known data tables, or creating a vacuum in the tank filled with liquid solvent and closing the tank and waiting until a thermodynamic equilibrium is established between the liquid and gaseous phases.

The initial pressure is for example about $10^{-5}$ Torr. As represented in FIG. 7, with reference to the particular embodiment of FIG. 5, first measurements are made during a time T, up to the time t1. The pressure remains constant throughout the measuring time T on account of pressure controller 11. Pressure controller 11 then controls the adsorption valve 5 and desorption valve 7, maintaining the continuous flow of solvent, to reach a pressure plateau P/Ps of higher value corresponding to another predetermined pressure value at which the measurements are made between times t1 and t2.

The measuring method then proceeds with control of the adsorption valve 5 and desorption valve 7 and regulation of the pressure at a succession of pressure plateaus of increasing values. At each pressure plateau P/Ps, the measuring time T is preferably identical and relatively short and the pressure remains constant.

After the succession of pressure plateaus P/Ps of increasing values, the pressure controller 11 can control the adsorption valve 5 and desorption valve 7 to regulate the pressure at a succession of pressure plateaus of decreasing values (not represented in FIG. 6 for the sake of clarity), corresponding to the desorption phase. The continuous flow of solvent between solvent tank 4 and pump 6 is maintained and the ellipsometry measurements are made during the same time period T, at constant pressure and on each pressure plateau. The predetermined pressure values of the plateaus of decreasing values are identical to those of the plateaus of increasing values, when the adsorption and desorption curves present the same form.

When the adsorption and desorption curves do not present the same form, the plateaus are selected according to the particular zones of each curve. For example, a large number of plateaus are chosen in the parts of the curve presenting a large gradient.

Measuring device 1, with pressure controller 11 controlling adsorption valve 5 and desorption valve 7, therefore enables the increasing and decreasing pressure plateaus to be finely controlled and precise and detailed isothermal curves to be constructed. For example, five successive pressure plateaus can be obtained for P/Ps values comprised between $10^{-7}$ and $10^{-3}$ to perform the ellipsometry measurements. The results obtained take a large number of measuring points into account and are very precise, as the pressure remains constant during the measuring time T. The isothermal curves obtained are then more reliable and usable in detail.

In the particular embodiment represented in FIG. 5, pressure controller 11 is itself controlled for example by a central control circuit 12 that is able to supply a specific pressure value, P setpoint. The controls f1(P) and f2(P) respectively of adsorption valve 5 and desorption valve 7 then depend on the pressure value P setpoint supplied and on the pressure value P measured by the pressure sensor 8.

In the particular embodiment represented in FIG. 6, pressure controllers 11a and 11b can also be controlled by a central control circuit 12 that is able to supply a specific pressure value, P setpoint, or they can be controlled individually by a corresponding control circuit (not represented).

For example, the adsorption valve 5 is controlled in position and the desorption valve 7 is controlled in pressure to obtain the continuous flow of solvent between tank 4 and pump 6. Inlet of solvent via adsorption valve 5 is performed by means of a micro-leak, preferably by means of a plurality of micro-leaks, for example of different sizes. Position control is performed by means of a mobile closing element, controlled by pressure controller 11 or by central control circuit 12, so that it blocks off the micro-leaks more or less. Pressure control of desorption valve 7 is performed by means of a more or less large opening of its desorption orifice.

For example, desorption valve 7 operates in the pressure stabilization phases and adsorption valve 5 in the pressure variation phases. At a first pressure value P1, desorption valve 7 is controlled by pressure controller 11 and adsorption valve 5 is blocked at a previously set opening. The solvent inlet is constant and the pumping is adjusted by desorption valve 7. The pressure is then stabilized at the first value P1. To reach a second pressure value P2, desorption valve 7 is fixed and the position of adsorption valve 5 varies. Once the second pressure value P2 is approached, adsorption valve 5 is fixed and pressure controller 11 controls desorption valve 7 according to the second value P2 as setpoint. The pressure is then stabilized at the second value P2.

For example, the principle is the same as before, but variation of the position of adsorption valve 5 is not necessary at each pressure plateau change. The complete range of physisorption pressures, approximately from $10^{-5}$ Torr to 50 Torr, is split into several sub-ranges, for example three or four, each corresponding to a position of adsorption valve 5, the sub-ranges being selected such as to remain in the optimum operating range of desorption valve 7.

In an alternative embodiment, solvent inlet by adsorption valve 5 can be performed by means of an injector. Pressure controller 11 then comprises means for controlling the quantity of solvent inlet to chamber 2 in order to calculate the exact quantity of solvent inlet to chamber 2. Pressure control of desorption valve 7 can also be performed by an injector, the latter enabling the exact quantity of solvent outlet from chamber 2 via desorption valve 7 to be controlled and quantified.

Figure 8:
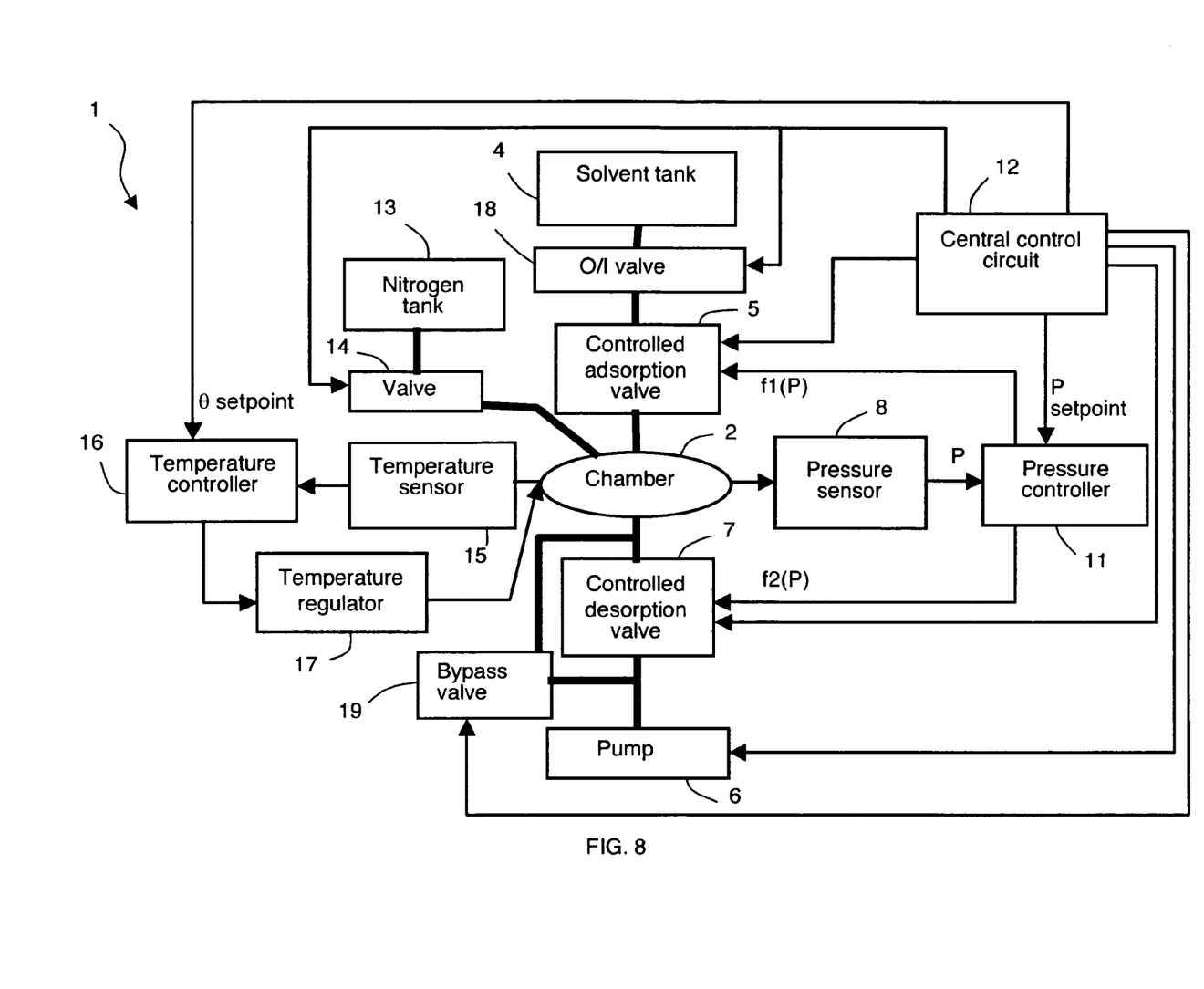
FIG. 8 represents another alternative embodiment of a device for measuring porosity by ellipsometry according to FIG. 5, in block diagram form.

In FIG. 8, the alternative embodiment of measuring device 1 differs from the previous embodiment by the presence of additional elements optimizing implementation of the measuring method. Measuring device 1 comprises a nitrogen tank 13 associated with an inlet valve 14 connected to an inlet of chamber 2.

Nitrogen tank 13 enables device 1 to perform a purging step of chamber 2 by means of nitrogen, before the vacuum pumping step initiating a cycle for measuring the porosity by ellipsometry. This purging step with nitrogen in particular enables any polluting molecules that may be present in chamber 2 to be removed to optimize the measurements that are subsequently made.

A nitrogen purging step can also advantageously be performed at the end of the measuring cycle, before chamber 2 is returned to atmospheric pressure before being opened to change element 3, in order to protect measuring device 1 from pollution when opening chamber 2.

In the particular embodiment of FIG. 8, measuring device 1 can comprise a temperature sensor 15 connected to a temperature controller 16 that is able to control and modify this temperature by means of a temperature regulator 17. Sensor 15, controller 16 and regulator 17 constitute a temperature control unit optimizing the precision and usability of the isothermal curves obtained after the measurements have been made. Keeping the temperature constant in fact makes sure that each operation has an isothermal nature and enables isothermal curves to be established that are usable at different temperatures and over the whole pressure range.

Temperature controller 16 may receive a setpoint temperature, $\theta$ setpoint, supplied for example by central control circuit 12 and corresponding to a predetermined temperature value for which the ellipsometric measurements have to be made.

The temperature is preferably measured on element 3 inside chamber 2 by means of a temperature sensor, for example a thermocouple or a thermoresistor, and regulated by a temperature regulator, for example of Peltier type.

In an alternative embodiment, it is the temperature inside chamber 2 that is measured and regulated. In this case, this control has to be scheduled when chamber 2 is designed, for example by inserting sensors inside chamber 2 advantageously as close as possible to element 3, for example at the level of an element holder or more generally at the level of the fixing means of element 3 in chamber 2.

In another alternative embodiment, the temperature can be measured and regulated at the level of the solvent tank 4. The temperature of the solvent is then modified before being inlet to chamber 2, for example by means of heating resistors inserted in solvent tank 4, or a heating coil containing a fluid at controlled temperature, situated around tank 4.

In the particular embodiment of measuring device 1 represented in FIG. 8, measuring device 1 can also comprise an on-off valve 18 fitted between solvent tank 4 and the corresponding adsorption valve 5. Valve 18 is designed to control full opening or full closing of solvent tank 4 to block the solvent flow from tank 4 or to let it pass. This on-off valve 18 is in particular used in the transition phases, such as initial pumping, purging with nitrogen, return to atmospheric pressure, and when a new element 3 is inserted in chamber 2, which must not contain any trace of solvent when transfer of the elements 3 is performed.

Measuring device 1 can also comprise a bypass valve 19 arranged between the outlet of chamber 2 and pump 6, enabling direct pumping of the solvent vapors without passing via the controlled desorption valve 7. Either the solvent vapors are intaken by controlled valve 7, in particular to regulate the pressure and ensure a continuous flow of solvent, or the solvent vapors are intaken by bypass valve 19 to remove a large quantity of solvent very quickly and without any control. Bypass valve 19 is notably used to drain chamber 2 before purging with nitrogen is performed, or when performing initial pumping to ensure a rapid drop to a relative vacuum and to prevent in particular carbonaceous pollution.

In another alternative embodiment, not represented, full automation of the measuring device 1 can be provided. Central control circuit 12 can for example be connected to a suitable computer which controls the temperature and pressure by means of servo-controls, for example of the Proportional Integral Derivative (PID) type. Depending on the predetermined pressure and temperature values, the computer recomputes the parameters and stabilizes the system in pressure and temperature by means of pressure controller 11 and temperature controller 16. The ellipsometric measurements can also be integrated in automatic control of the parameters controlled by the computer.

Such a measuring device 1, according to the different embodiments described above, enables a method of measuring porosity by ellipsometry to be implemented controlling and regulating the pressure or the temperature. The measurements can thus be made at variable pressure and constant temperature (isothermal adsorption). In this case, the relative pressure is successively regulated to different predetermined values by regulating the pressure to different successive values. For example, using ethanol as solvent and for a pressure of about 0.001 Torr to 1 Torr, the relative pressure at 20° C. varies respectively from $2.3*10^{-5}$ to $2.3*10^{-2}$, the relative pressure at 30° C. varies respectively from $1.3*10^{-5}$ to $1.3*10^{-2}$, the relative pressure at 40° C. varies respectively from $7.5*10^{-6}$ to $7.5*10^{-3}$, the relative pressure at 50° C. varies respectively from $4.5*10^{-6}$ to $4.5*10^{-3}$ and the relative pressure at 60° C. varies respectively from $2.85*10^{-6}$ to $2.85*10^{-3}$.

Control and stabilization of the temperature thereby make the results of the isothermal adsorption and desorption cycles more reliable. The possibility of stabilizing at different temperatures, for example 20° C., 30° C., 40° C., 50° C., 60° C., enables certain pressure ranges, in particular low pressures, to be more precisely detailed. For example, whereas at 20° C. the relative pressure can vary from $2.3*10^{-5}$ to $2.3*10^{-2}$, at 60° C. the relative pressure can vary from $2.85*10^{-6}$ to $2.85*10^{-2}$.

Measurements can also be made at constant pressure and variable temperature (isobaric adsorption). In this case, the relative pressure is in particular successively regulated to different predetermined values by modifying the value of the saturated vapor pressure Ps, and regulating the temperature to different predetermined values. For example, using ethanol as solvent and for a temperature of about 20° C., 30° C., 40° C., 50° C., 60° C., the saturated vapor pressure Ps is respectively about 44 Torr, 78 Torr, 133.7 Torr, 220 Torr, 350.3 Torr. The temperature increase thereby enables low relative pressures to be reached and detailed simply by increasing the saturated vapor pressure Ps, without changing the pressure setpoint P. For example, for a pressure of about 0.001 Torr, the relative pressure is about $2.3*10^{-5}$ (20° C.), $1.3*10^{-5}$ (30° C.), $7.5*10^{-8}$ (40° C.), $4.5*10^{-6}$ (50° C.), $2.85*10^{-6}$ (60° C.) and, for a pressure of about 0.1 Torr, the relative pressure is about $2.3*10^{-3}$ (20° C.), $1.3*10^{-3}$ (30° C.), $7.5*10^{-4}$ (40° C.), $4.5*10^{-4}$ (50° C.) and $2.85*10^{-4}$ (60° C.).

Dynamic pressure management, i.e. maintaining a constant flow of solvent in the chamber, thus makes it possible to maintain a stable pressure in the chamber, while making the temperature vary at selected values. Increasing or reducing the temperature will then influence desorption or adsorption of the solvent. The theoretical isothermal physisorption models, for example Kelvin, Dubinin-Radushkevich, are then adapted to isobaric physisorption.

In all cases, pressure control, possibly coupled with temperature control, notably enables reliable and usable isothermal curves to be obtained over the whole pressure range and at different temperatures. It is possible to increase the number of measuring points and to have a finer control of the pressure plateaus, so as to perform in-depth analysis of the results.

Controlling the continuous flow of solvent, by controlling the adsorption 5 and desorption 7 valves, also achieves an enhanced precision as far as the pressure is concerned, in particular in the low pressure range, to be able to characterize the microporosity.

The measuring device also enables the impact of pollution and of possible leaks of chamber 2 on the measurements to be limited, by continuous removal of pollutants.

Computer control of the pressure and temperature parameters if performed also provides a flexibility of use and a great precision (number of measurements, pressure range, etc.) adapted to the different possible uses. Measurements and studies of materials are greatly facilitated.

The invention is not limited to the different embodiments described above. Determination of the pressure value P setpoint can be directly integrated in pressure controller 11 (FIG. 5) or 11a, 11b (FIG. 6). Other types of servo-control can be used, in case of automation of the measuring device 1, so long as they are precise and efficient.

Control of adsorption valve 5 can be performed according to the pressure, and control of desorption valve 7 can be performed according to the position of a closing element designed to more or less block off one or more micro-leaks of desorption valve 7.

Pressure sensor 8 can be replaced by an assembly comprising two membrane gauges performing strict control of the pressure over the whole pressure range ($10^{-5}$ to 100 Torr).

Control of adsorption valve 5 and desorption valve 7 can be performed by means of two flow controllers, i.e. one for solvent inlet and the other for solvent pumping.

It is possible to provide an additional bypass valve between solvent tank 4 and an inlet of chamber 2 to perform controlled inlet of the solvent to chamber 2, in particular to place solvent tank 4 at saturated vapor pressure.

In another alternative embodiment, not represented, an intermediate chamber for inlet of elements 3 can be provided, for example a transition chamber designed to condition element 3 before the latter is inlet to chamber 2. Such a pressurization chamber in particular enables carbonaceous pollution of the porous materials to be limited, chamber 2 remaining under vacuum during transition between two elements 3.

The invention claimed is:

1. A method for measuring the porosity of an element by means of a device comprising:
    a measuring chamber in which the element is disposed,
    a solvent tank associated with an adsorption valve, arranged between the solvent tank and an inlet of the chamber,
    a pump associated with a desorption valve, arranged between an outlet of the chamber and the pump,
    a pressure sensor,
    and control means for controlling the adsorption and desorption valves,
    said measuring method comprising measurement of the pressure in the chamber by means of the pressure sensor, and a measuring cycle for measuring the porosity by ellipsometry, at different predetermined pressure, wherein, during the cycle for measuring the porosity by ellipsometry, said control means control opening of the adsorption and desorption valves according to the measured pressure, the relative pressure in the chamber being successively regulated to different predetermined values, while maintaining a continuous flow of solvent in the chamber between the tank and the pump.

2. The method according to claim 1, wherein the relative pressure is successively regulated at different predetermined values by modifying the saturated vapor pressure, by regulating the temperature to different successive values, at constant pressure.

3. The method according to claim 1, comprising pumping of the chamber by means of the pump until a relative vacuum is achieved, before the cycle for measuring the porosity by ellipsometry.

4. The method according to claim 3, comprising a purging step of the chamber with nitrogen, before the pumping step of the chamber to achieve the relative vacuum.

5. The method according to claim 1, wherein the relative pressure is successively regulated to different predetermined values by regulating the pressure to different successive values, at constant temperature.

6. The method according to claim 5, wherein, during the cycle for measuring the porosity by ellipsometry, the control means control opening of the adsorption and desorption valves so as to form a succession of successive pressure plateaus of increasing values.

7. The method according to claim 5, wherein, during the cycle for measuring the porosity by ellipsometry, the control means control opening of the adsorption and desorption valves so as to form a succession of successive pressure plateaus of decreasing values.

8. The method according to claim 1, comprising measurement and regulation of the temperature, during the cycle for measuring the porosity by ellipsometry.

9. The method according to claim 8, wherein the temperature is measured on the element inside the chamber by means of a thermocouple or a thermoresistor and regulated by a Peltier type temperature controller.

10. The method according to claim 8, wherein the temperature is measured and regulated at the level of the chamber.

11. The method according to claim 8, wherein the measured and regulated temperature is the temperature of the solvent before the latter is inlet to the chamber.

12. A device for implementing the measuring method according to claim 1, wherein the adsorption and desorption valves are controlled in pressure or in position, by means of the control means controlling opening of the valves.

13. The device according to claim 12, wherein at least one of the valves comprises at least one micro-leak, said control means controlling opening of said valves comprising control means of the position of a closing element of said micro-leaks.

14. The device according to claim 12, wherein at least one of the valves comprises an injector, said control means controlling opening of said valves comprising control means of the quantity of solvent flowing in said injector.

* * * * *